United States Patent
Ferrari et al.

(10) Patent No.: US 10,729,058 B2
(45) Date of Patent: Aug. 4, 2020

(54) SYSTEMS AND METHODS FOR ADJUSTING THE OUTPUT OF A FIELD MEASUREMENT SYSTEM TO CONFORM TO AGRONOMY MEASUREMENTS

(71) Applicants: CNH Industrial Canada, Ltd., Saskatoon (CA); Autonomous Solutions, Inc., Mendon, UT (US)

(72) Inventors: Luca Ferrari, Modena (IT); John H. Posselius, Ephrata, PA (US); James W. Henry, Saskatoon (CA); Taylor C. Bybee, Logan, UT (US); Bret T. Turpin, Wellsville, UT (US)

(73) Assignees: CNH Industrial Canada, Ltd., Saskatoon, Saskatchewan (CA); Autonomous Solutions, Inc., Mendon, UT (US)

( * ) Notice: Subject to any disclaimer, the term of this patent is extended or adjusted under 35 U.S.C. 154(b) by 131 days.

(21) Appl. No.: 16/015,720

(22) Filed: Jun. 22, 2018

(65) Prior Publication Data
US 2019/0387659 A1    Dec. 26, 2019

(51) Int. Cl.
*A01B 79/00* (2006.01)
*A01B 76/00* (2006.01)
*G01N 33/24* (2006.01)
*G01N 33/00* (2006.01)

(52) U.S. Cl.
CPC ............ *A01B 79/005* (2013.01); *A01B 76/00* (2013.01); *G01N 33/0098* (2013.01); *G01N 33/24* (2013.01); *G01N 2033/245* (2013.01)

(58) Field of Classification Search
None
See application file for complete search history.

(56) References Cited

U.S. PATENT DOCUMENTS

| | | | |
|---|---|---|---|
| 6,041,582 A | 3/2000 | Tiede et al. | |
| 9,282,688 B2 | 3/2016 | Casper et al. | |
| 9,629,304 B2 | 4/2017 | Zielke | |
| 9,891,629 B2 | 2/2018 | Murray et al. | |
| 2015/0302305 A1 | 10/2015 | Rupp et al. | |
| 2018/0014452 A1 | 1/2018 | Starr | |

*Primary Examiner* — Abdhesh K Jha
(74) *Attorney, Agent, or Firm* — Rebecca L. Henkel; Rickard K. DeMille

(57) ABSTRACT

The present disclosure provides systems and methods for adjusting the output of a field measurement system to conform to agronomy measurements. In particular, the present subject matter is directed to a calibration process and system that uses a calibration model to convert field measurement data expressed according to an automatic system metric into agronomy data that is expressed according to an agronomy metric.

19 Claims, 5 Drawing Sheets

SYSTEMS AND METHODS FOR ADJUSTING THE OUTPUT OF A FIELD MEASUREMENT SYSTEM TO CONFORM TO AGRONOMY MEASUREMENTS

FIELD OF THE INVENTION

The present subject matter relates generally to agricultural field measurement systems and, more particularly, to systems and methods for adjusting the output of a field measurement system to conform to agronomy measurements.

BACKGROUND OF THE INVENTION

Various types of field measurements provide important data regarding the conditions in a field, including the environmental and/or seed-bed conditions in a field. For example, field measurements can include crop residue measurements (e.g., percent crop residue cover), soil roughness measurements (e.g., measurements of average soil clod size or the like), and/or other measurements of a field and its characteristics. These measurements are of high value to agricultural operators to understand current conditions of the field and, if needed, to modify the conditions of the field to be more optimal.

As one example, for various reasons, it is important to maintain a given amount of crop residue within a field following an agricultural operation. Specifically, crop residue remaining within the field can help in maintaining the content of organic matter within the soil and can also serve to protect the soil from wind and water erosion. However, in some cases, leaving an excessive amount of crop residue within a field can have a negative effect on the soil's productivity potential, such as by slowing down the warming of the soil at planting time and/or by slowing down seed germination. As such, the ability to monitor and/or adjust the amount of crop residue remaining within a field can be very important to maintaining a healthy, productive field, particularly when it comes to performing tillage operations.

As another example, for various reasons, it is important to maintain a given amount of soil roughness within a field before or following an agricultural operation. For example, when planting seeds it is generally not desired to have soil clods that are larger than a certain size.

In the past, these field measurements have been manually generated by a human operator/planter. More recently, automatic field measurement systems have been developed that generate these field measurements automatically or in a partially-automated fashion. Typically these automatic field measurement systems deploy or otherwise leverage a number of sensors, such as vision sensors, to produce the field measurements.

In particular, these automatic field measurement systems typically provide field measurement data expressed according to an automatic system metric associated with the automatic field measurement system. However, this automatic system metric may not accurately scale with established agronomical measurements. Thus, the output of the automatic field measurement system may be confusing or otherwise difficult to use due to its failure to scale accurately with more established agronomy metrics promulgated by various agronomy experts or organizations.

BRIEF DESCRIPTION OF THE INVENTION

Aspects and advantages of the invention will be set forth in part in the following description, or may be obvious from the description, or may be learned through practice of the invention.

One example aspect of the present disclosure is directed to a computer-implemented method for calibrating automatic field measurements. The method includes receiving, with a computing device, field measurement data generated by an automatic field measurement system, wherein the field measurement data generated by the automatic field measurement system is expressed according to an automatic system metric associated with the automatic field measurement system. The method includes accessing, with the computing device, a calibration model that describes a relationship between the automatic system metric associated with the automatic field measurement system and an agronomy metric. The agronomy metric is different from the automatic system metric. The method includes using, with the computing device, the calibration model to convert the field measurement data expressed according to the automatic system metric into agronomy data expressed according to the agronomy metric.

Another example aspect of the present disclosure is directed to a computing system for calibrating automatic field measurements. The computing system includes one or more processors and one or more non-transitory computer-readable media that collectively store a calibration model that describes a relationship between an automatic system metric associated with an automatic field measurement system and an agronomy metric. The agronomy metric is different from the automatic system metric. The one or more non-transitory computer-readable media collectively store instructions that, when executed by the one or more processors, cause the computing system to perform operations. The operations include receiving field measurement data generated by the automatic field measurement system. The field measurement data generated by the automatic field measurement system is expressed according to the automatic system metric associated with the automatic field measurement system. The operations include accessing the calibration model that describes the relationship between the automatic system metric associated with the automatic field measurement system and the agronomy metric. The operations include using the calibration model to convert the field measurement data expressed according to the automatic system metric into agronomy data expressed according to the agronomy metric.

Another example aspect of the present disclosure is directed to an agricultural work vehicle or agricultural implement that includes an automatic field measurement system configured to generate field measurement data descriptive of an agricultural field. The field measurement data generated by the automatic field measurement system is expressed according to an automatic system metric associated with the automatic field measurement system. The agricultural work vehicle or agricultural implement includes a calibration computing system configured to: receive the field measurement data generated by the automatic field measurement system; access a calibration model that describes a relationship between the automatic system metric associated with the automatic field measurement system and an agronomy metric, wherein the agronomy metric is different from the automatic system metric; and use the calibration model to convert the field measurement data expressed according to the automatic system metric into agronomy data expressed according to the agronomy metric.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
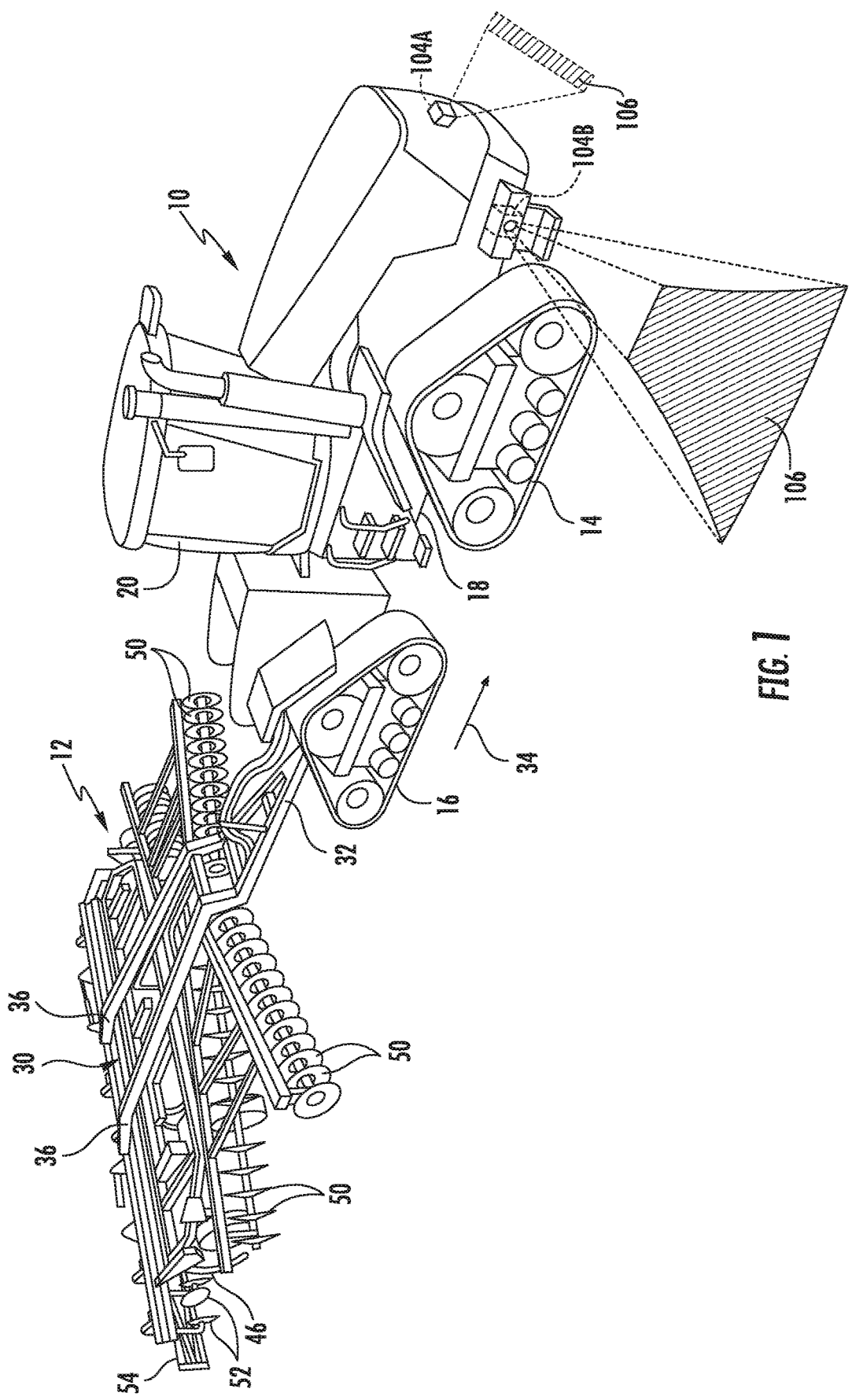
FIG. 1 illustrates a perspective view of one embodiment of a work vehicle towing an implement in accordance with aspects of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and methods for adjusting the output of a field measurement system to conform to agronomy measurements. In particular, the present subject matter is directed to a calibration process and system that uses a calibration model to convert field measurement data expressed according to an automatic system metric into agronomy data that is expressed according to an agronomy metric.

More particularly, as described above, an automatic field measurement system can produce field measurement data that is expressed according to an automatic system metric associated with the automatic field measurement system. As examples, the field measurement data can include crop residue data, soil roughness data, and/or other measurements of field conditions or characteristics.

However, this automatic system metric may not accurately scale with established agronomical measurements. For example, the automatic system may output crop residue in a logarithmic scale while an agronomist measures in a linear scale. Thus, the output of the automatic field measurement system may be confusing or otherwise difficult to use due to its failure to scale accurately with more established agronomy metrics promulgated by various agronomy experts or organizations.

As such, the present disclosure provides systems and methods that perform a calibration from one scale to another. In particular, in one example, a computing system can receive field measurement data generated by an automatic field measurement system and expressed according to an automatic system metric associated with the automatic field measurement system. The computing system can access a calibration model that describes a relationship between the automatic system metric associated with the automatic field measurement system and an agronomy metric, wherein the agronomy metric is different from the automatic system metric. The computing system can use the calibration model to convert the field measurement data expressed according to the automatic system metric into agronomy data expressed according to the agronomy metric.

The calibration model used by the systems and methods of the present disclosure can have a number of different forms or structures. As one example, the calibration model can perform or include a least squares polynomial fit that describes the relationship between the automatic system metric and the agronomy metric according to a polynomial expression. As another example, the calibration model can include or use a look up table that provides an agronomy data value for each possible field measurement data value. As yet another example, the calibration model can perform or include a Gaussian Process regression that describes the relationship between the automatic system metric and the agronomy metric As another example, the calibration model can be or include a spline or otherwise piece-wise function that describes the relationship between the automatic system metric and the agronomy metric. As yet another example, the calibration model can convert field measurement data expressed according to a logarithmic scale into agronomy data expressed according to a linear scale.

Thus, in some embodiments, the calibration process can be combined with an existing field measurement system or algorithm. In other embodiments, the calibration process can be co-developed with a field measurement algorithm. By removing the agronomy calibration out of such field measurement algorithm (that is, separating the two problems and allowing the calibration process to handle agronomy calibration) the development of the field measurement algorithm can be greatly simplified, thereby likely leading to superior results. Furthermore, existing or newly developed field measurement algorithms (which may, for example, be analytical or heuristic algorithms) may exhibit bias in the algorithms (e.g., due to bias in the underlying data). Thus, in some embodiments, use of the calibration layer may also be able to correct or account for bias exhibited by the underlying field measurement algorithm. As such, in some embodiments, the calibration system and process can be viewed as an additional calibration layer that recalibrates a measurement algorithm that is otherwise accurate.

In some embodiments, the calibration systems and methods of the present disclosure can convert the field measurement data according to one of a number of different agronomy metrics. For example, a plurality of different agronomy metrics may be promulgated by different agronomists or agronomy organizations and certain of such different agronomy metrics may be preferred or used by some agricultural operators while other metrics are preferred or used by other agricultural operators. In some embodiments, a user can select one of such plurality of different agronomy metrics and the calibration system can convert the field measurement data into agronomy data expressed according to or in accordance with the selected agronomy metric.

In some embodiments, the calibration systems and methods of the present disclosure can convert the field measurement data according to one of a number of different agronomy metrics that are specifically associated with different geographic areas and/or different soil types or materials (e.g., that are associated with the different geographic areas). For example, a plurality of different agronomy metrics may be promulgated, where each agronomy metric is designed for or otherwise specific to a different geographic area and/or different mix of soil types or materials. In some embodiments, a user can select one of such plurality of different agronomy metrics and the calibration system can convert the field measurement data into agronomy data expressed according to or in accordance with the selected agronomy metric. In other embodiments, the calibration system can automatically select the particular agronomy metric into which the field measurement data is converted based on available information including, for example, location information (e.g., GPS data), humidity information, date or time of day information, imagery of the soil, and/or other types of data.

Furthermore, in some embodiments, an operation of an agricultural work vehicle or implement can be controlled based at least in part on the agronomy data. For example, the automatic field measurement system and/or the calibration computing device can be physically located on-board the at least one of the work vehicle or the implement and the calibration can be performed in real-time as part of a control feedback loop that controls operations of the vehicle or implement in real-time based on the field measurements expressed according to the agronomy metric. As examples, the relative positioning, penetration depth, down force, and/or any other operational parameters associated with one or more ground-engaging tools can be modified based on the agronomy data, thereby modifying the field conditions within the field towards a target condition. Thus, the systems and methods of the present disclosure can enable improved real-time control that measures and accounts for existing field conditions during field operations.

Through the use of a calibration model to convert field measurements into agronomy data, the systems and methods of the present disclosure can produce field measurements that are more easily understandable to operators of automatic field measurement systems. For example, the calibration process can be performed to enable automatic field measurements to scale appropriately with agronomy metrics with which the agricultural operator may be more familiar or with which existing implements or systems may be designed to operate, thereby enabling improved integration of the automatic field measurement system with existing systems or structures. This improved understandability and integration can enable improved and/or more precise control of the work vehicle and/or implement to obtain a desired field condition (e.g., residue cover and/or soil roughness) within a field and, as a result, lead to superior agricultural outcomes.

Figure 2:
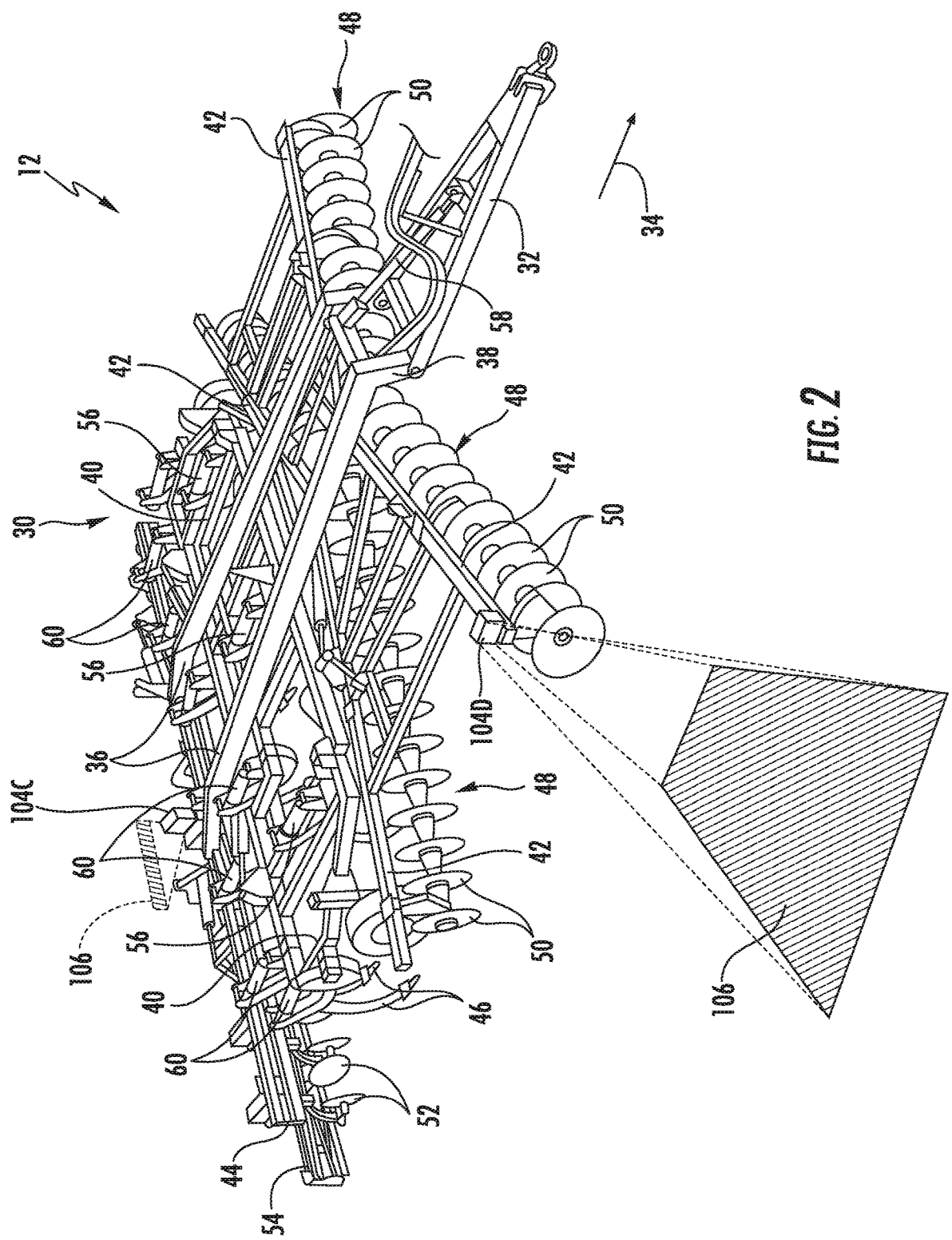
FIG. 2 illustrates a perspective view of the implement shown in FIG. 1.

Referring now to drawings, FIGS. 1 and 2 illustrate perspective views of one embodiment of a work vehicle 10 and an associated agricultural implement 12 in accordance with aspects of the present subject matter. Specifically, FIG. 1 illustrates a perspective view of the work vehicle 10 towing the implement 12 (e.g., across a field). Additionally, FIG. 2 illustrates a perspective view of the implement 12 shown in FIG. 1. As shown in the illustrated embodiment, the work vehicle 10 is configured as an agricultural tractor. However, in other embodiments, the work vehicle 10 may be configured as any other suitable agricultural vehicle.

As particularly shown in FIG. 1, the work vehicle 10 includes a pair of front track assemblies 14, a pair of rear track assemblies 16 and a frame or chassis 18 coupled to and supported by the track assemblies 14, 16. An operator's cab 20 may be supported by a portion of the chassis 18 and may house various input devices for permitting an operator to control the operation of one or more components of the work vehicle 10 and/or one or more components of the implement 12. Additionally, as is generally understood, the work vehicle 10 may include an engine 22 (FIG. 3) and a transmission 24 (FIG. 3) mounted on the chassis 18. The transmission 24 may be operably coupled to the engine 22 and may provide variably adjusted gear ratios for transferring engine power to the track assemblies 14, 16 via a drive axle assembly (not shown) (or via axles if multiple drive axles are employed).

Moreover, as shown in FIGS. 1 and 2, the implement 12 may generally include a carriage frame assembly 30 configured to be towed by the work vehicle via a pull hitch or tow bar 32 in a travel direction of the vehicle (e.g., as indicated by arrow 34). The carriage frame assembly 30 may be configured to support a plurality of ground-engaging tools, such as a plurality of shanks, disk blades, leveling blades, basket assemblies, and/or the like. In several embodiments, the various ground-engaging tools may be configured to perform a tillage operation across the field along which the implement 12 is being towed.

As particularly shown in FIG. 2, the carriage frame assembly 30 may include aft extending carrier frame members 36 coupled to the tow bar 32. In addition, reinforcing gusset plates 38 may be used to strengthen the connection between the tow bar 32 and the carrier frame members 36. In several embodiments, the carriage frame assembly 30 may generally function to support a central frame 40, a forward frame 42 positioned forward of the central frame 40 in the direction of travel 34 of the work vehicle 10, and an aft frame 44 positioned aft of the central frame 40 in the direction of travel 34 of the work vehicle 10. As shown in FIG. 2, in one embodiment, the central frame 40 may correspond to a shank frame configured to support a plurality of ground-engaging shanks 46. In such an embodiment, the shanks 46 may be configured to till the soil as the implement 12 is towed across the field. However, in other embodiments, the central frame 40 may be configured to support any other suitable ground-engaging tools.

Additionally, as shown in FIG. 2, in one embodiment, the forward frame 42 may correspond to a disk frame configured to support various gangs or sets 48 of disk blades 50. In such an embodiment, each disk blade 50 may, for example, include both a concave side (not shown) and a convex side (not shown). In addition, the various gangs 48 of disk blades 50 may be oriented at an angle relative to the travel direction 34 of the work vehicle 10 to promote more effective tilling of the soil. However, in other embodiments, the forward frame 42 may be configured to support any other suitable ground-engaging tools.

As another example, ground-engaging tools can include harrows which can include, for example, a number of tines or spikes, which are configured to level or otherwise flatten any windrows or ridges in the soil. The implement 12 may include any suitable number of harrows. In fact, some embodiments of the implement 12 may not include any harrows.

In some embodiments, the implement 12 may optionally include one or more additional ground-engaging tools, such as one or more basket assemblies or rotary firming wheels. The baskets may be configured to reduce the number of clods in the soil and/or firm the soil over which the implement 12 travels. Each basket may be configured to be pivotally coupled to one of the frames 40, 42, 44, or other components of the implement 12. It should be appreciated that the implement 12 may include any suitable number of baskets. In fact, some embodiments of the implement 12 may not include any baskets.

Moreover, similar to the central and forward frames 40, 42, the aft frame 44 may also be configured to support a plurality of ground-engaging tools. For instance, in the illustrated embodiment, the aft frame is configured to support a plurality of leveling blades 52 and rolling (or crumbler) basket assemblies 54. However, in other embodiments, any other suitable ground-engaging tools may be coupled to and supported by the aft frame 44, such as a plurality of closing disks.

In addition, the implement 12 may also include any number of suitable actuators (e.g., hydraulic cylinders) for adjusting the relative positioning, penetration depth, and/or down force associated with the various ground-engaging tools (e.g., ground-engaging tools 46, 50, 52, 54). For instance, the implement 12 may include one or more first actuators 56 coupled to the central frame 40 for raising or lowering the central frame 40 relative to the ground, thereby allowing the penetration depth and/or the down pressure of the shanks 46 to be adjusted. Similarly, the implement 12 may include one or more second actuators 58 coupled to the disk forward frame 42 to adjust the penetration depth and/or the down pressure of the disk blades 50. Moreover, the implement 12 may include one or more third actuators 60 coupled to the aft frame 44 to allow the aft frame 44 to be moved relative to the central frame 40, thereby allowing the relevant operating parameters of the ground-engaging tools 52, 54 supported by the aft frame 44 (e.g., the down pressure and/or the penetration depth) to be adjusted.

It should be appreciated that the configuration of the work vehicle 10 described above and shown in FIG. 1 is provided only to place the present subject matter in an exemplary field of use. Thus, it should be appreciated that the present subject matter may be readily adaptable to any manner of work vehicle configuration. For example, in an alternative embodiment, a separate frame or chassis may be provided to which the engine, transmission, and drive axle assembly are coupled, a configuration common in smaller tractors. Still other configurations may use an articulated chassis to steer the work vehicle 10, or rely on tires/wheels in lieu of the track assemblies 14, 16.

It should also be appreciated that the configuration of the implement 12 described above and shown in FIGS. 1 and 2 is only provided for exemplary purposes. Thus, it should be appreciated that the present subject matter may be readily adaptable to any manner of implement configuration. For example, as indicated above, each frame section of the implement 12 may be configured to support any suitable type of ground-engaging tools, such as by installing closing disks on the aft frame 44 of the implement 12 or other modifications.

Additionally, in accordance with aspects of the present subject matter, the work vehicle 10 and/or the implement 12 may include or have associated therewith an automatic field measurement system. The automatic field measurement system can automatically or in an at least partially-automated fashion generate field measurement data that includes measurements of one or more conditions of a field. Example conditions of a field include crop residue conditions (e.g., percent crop residue cover), soil roughness conditions (e.g., average soil clod size, clod density, or other roughness characteristics), and/or other measures of various conditions or characteristics of a field.

Generally, the automatic field measurement system can include one or more sensors (e.g., as shown at 121 in FIG. 3) that generate data that can be processed to measure the field conditions. The sensors can be any type of sensors including depth sensors, humidity sensors, temperature sensors, surface roughness sensors, vision sensors such as imaging device, acoustic sensors, and/or other types of sensors.

Thus, in some embodiments, as illustrated in FIGS. 1 and 2, the work vehicle 10 and/or the implement 12 may have one or more imaging devices coupled thereto and/or supported thereon for capturing images or other image data associated with the field as an operation is being performed via the implement 12. Specifically, in several embodiments, the imaging device(s) may be provided in operative association with the work vehicle 10 and/or the implement 12 such that the imaging device(s) has a field of view directed towards a portion(s) of the field disposed in front of, behind, and/or underneath some portion of the work vehicle 10 and/or implement 12 such as, for example, alongside one or both of the sides of the work vehicle 10 and/or the implement 12 as the implement 12 is being towed across the field. As such, the imaging device(s) may capture images from the tractor 10 and/or implement 12 of one or more portion(s) of the field being passed by the tractor 10 and/or implement 12.

In general, the imaging device(s) may correspond to any suitable device(s) configured to capture images or other image data of the field that allow the field's soil to be distinguished from the crop residue remaining on top of the soil. For instance, in several embodiments, the imaging device(s) may correspond to any suitable camera(s), such as single-spectrum camera or a multi-spectrum camera configured to capture images, for example, in the visible light range and/or infrared spectral range. Additionally, in a particular embodiment, the camera(s) may correspond to a single lens camera configured to capture two-dimensional images or a stereo camera(s) having two or more lenses with a separate image sensor for each lens to allow the camera(s) to capture stereographic or three-dimensional images. Alternatively, the imaging device(s) may correspond to any other suitable image capture device(s) and/or vision system(s) that is capable of capturing "images" or other image-like data that allow the crop residue existing on the soil to be distinguished from the soil. For example, the imaging device(s) may correspond to or include radio detection and ranging (RADAR) sensors and/or light detection and ranging (LIDAR) sensors.

It should be appreciated that work vehicle 10 and/or implement 12 may include any number of imaging device(s) 104 or other sensors provided at any suitable location that allows images of the field to be captured as the vehicle 10 and implement 12 traverse through the field. For instance, FIGS. 1 and 2 illustrate examples of various locations for mounting one or more imaging device(s) for capturing images of the field. Specifically, as shown in FIG. 1, in one embodiment, one or more imaging devices 104A may be coupled to the front of the work vehicle 10 such that the imaging device(s) 104A has a field of view 106 that allows it to capture images of an adjacent area or portion of the field disposed in front of the work vehicle 10. For instance, the field of view 106 of the imaging device(s) 104A may be directed outwardly from the front of the work vehicle 10 along a plane or reference line that extends generally parallel to the travel direction 34 of the work vehicle 10. In addition to such imaging device(s) 104A (or as an alternative thereto), one or more imaging devices 104B may also be coupled to one of the sides of the work vehicle 10 such that the imaging device(s) 104B has a field of view 106 that allows it to capture images of an adjacent area or portion of the field disposed along such side of the work vehicle 10. For instance, the field of view 106 of the imaging device(s) 104B may be directed outwardly from the side of the work vehicle 10 along a plane or reference line that extends generally perpendicular to the travel direction 34 of the work vehicle 10.

Similarly, as shown in FIG. 2, in one embodiment, one or more imaging devices 104C may be coupled to the rear of the implement 12 such that the imaging device(s) 104C has a field of view 106 that allows it to capture images of an adjacent area or portion of the field disposed aft of the implement. For instance, the field of view 106 of the imaging device(s) 104C may be directed outwardly from the rear of the implement 12 along a plane or reference line that extends generally parallel to the travel direction 34 of the work vehicle 10. In addition to such imaging device(s) 104C (or as an alternative thereto), one or more imaging devices 104D may also be coupled to one of the sides of the implement 12 such that the imaging device(s) 104D has a field of view 106 that allows it to capture images of an adjacent area or portion of the field disposed along such side of the implement 12. For instance, the field of view 106 of the imaging device 104D may be directed outwardly from the side of the implement 12 along a plane or reference line that extends generally perpendicular to the travel direction 34 of the work vehicle 10.

It should be appreciated that, in alternative embodiments, the imaging device(s) 104 may be installed at any other suitable location that allows the device(s) to capture images of an adjacent portion of the field, such as by installing an imaging device(s) at or adjacent to the aft end of the work vehicle 10 and/or at or adjacent to the forward end of the implement 12. It should also be appreciated that, in several embodiments, the imaging devices 104 may be specifically installed at locations on the work vehicle 10 and/or the implement 12 to allow images to be captured of the field both before and after the performance of a field operation by the implement 12. For instance, by installing the imaging device 104A at the forward end of the work vehicle 10 and the imaging device 104C at the aft end of the implement 12, the forward imaging device 104A may capture images of the field prior to performance of the field operation while the aft imaging device 104C may capture images of the same portions of the field following the performance of the field operation.

Figure 3:
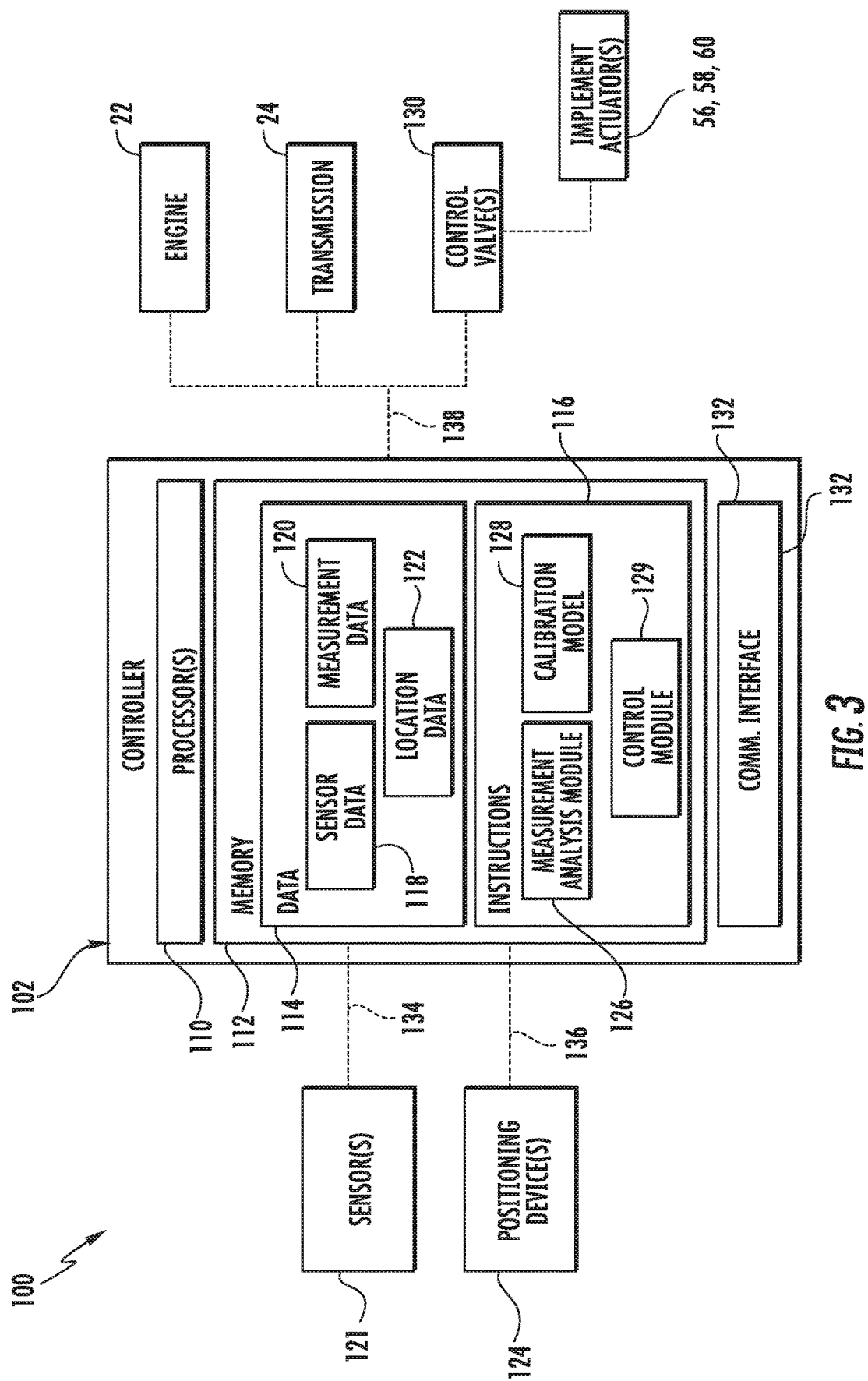
FIG. 3 illustrates a schematic view of one embodiment of a computing system in accordance with aspects of the present subject matter.
Figure 4:
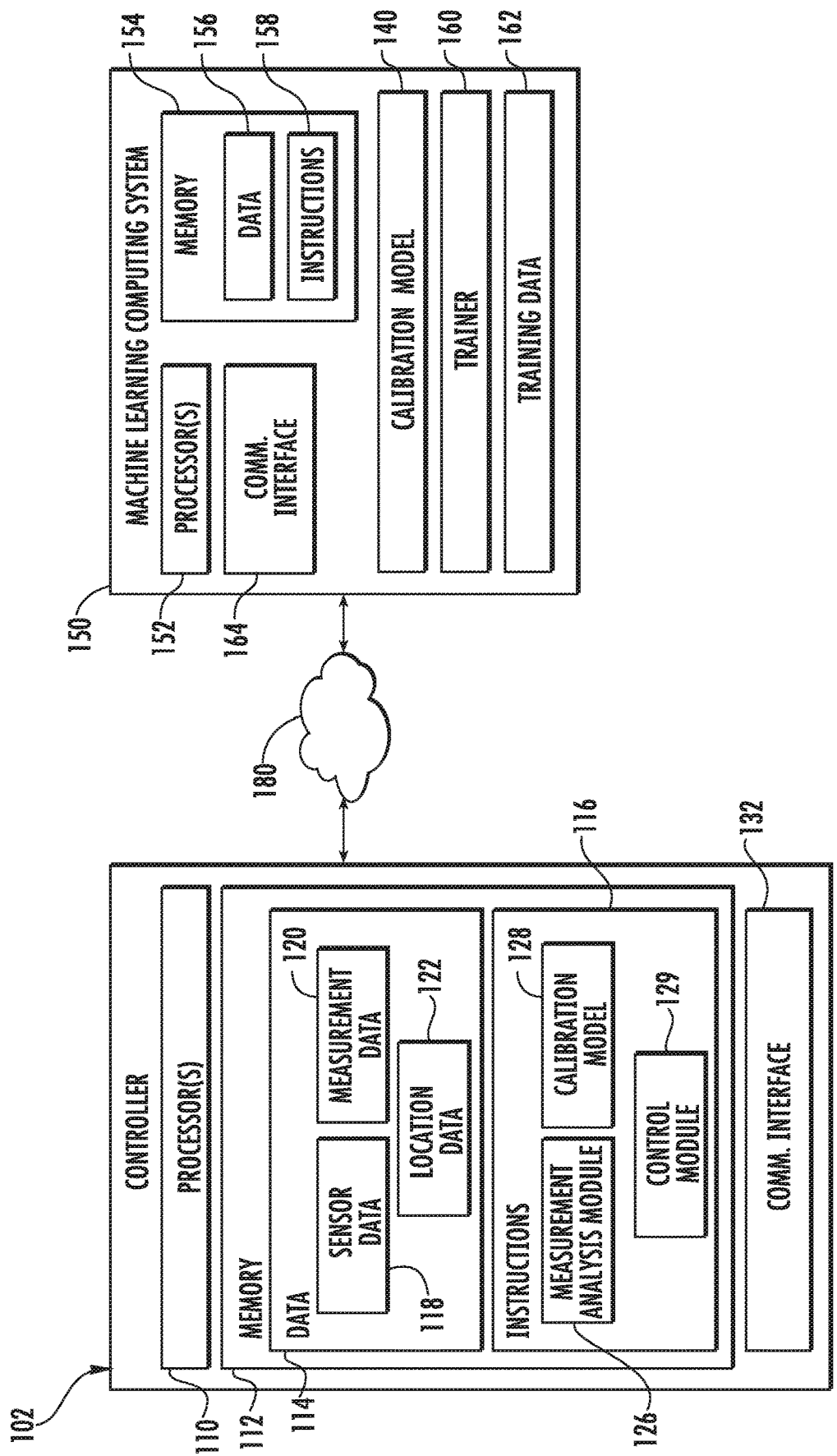
FIG. 4 illustrates a schematic view of one embodiment of a computing system in accordance with aspects of the present subject matter.

Referring now to FIGS. 3 and 4, schematic views of embodiments of a computing system 100 are illustrated in accordance with aspects of the present subject matter. In general, the system 100 will be described herein with reference to the work vehicle 10 and the implement 12 described above with reference to FIGS. 1 and 2. However, it should be appreciated that the disclosed system 100 may generally be utilized with work vehicles having any suitable vehicle configuration and/or implements have any suitable implement configuration.

In several embodiments, the system 100 may include a controller 102 and various other components configured to be communicatively coupled to and/or controlled by the controller 102, such as one or more sensors 121 and/or various components of the work vehicle 10 and/or the implement 12. In some embodiments, the controller 102 is physically coupled to the work vehicle 10 and/or the implement 12. In other embodiments, the controller 102 is not physically coupled to the work vehicle 10 and/or the implement 12 (e.g., remotely located from the work vehicle 10 and/or the implement 12) and instead may communicate with the work vehicle 10 and/or the implement 12 over a wireless network.

As will be described in greater detail below, the controller 102 may be configured to generate automatic field measurements and convert the automatic field measurements to agronomy data. In particular, FIG. 3 illustrates a computing environment in which the controller 102 can operate to generate measurement data 120 based on sensor data newly received from one or more sensors 121. That is, FIG. 3 illustrates a computing environment in which the controller 102 is actively used in conjunction with a work vehicle and/or implement (e.g., during operation of the work vehicle and/or implement within a field). As will be discussed further below, FIG. 4 depicts a computing environment in which the controller 102 can communicate over a network 180 with a machine learning computing system 150 to train and/or receive a calibration model 128. Thus, FIG. 4 illustrates operation of the controller 102 to train a calibration model 128 and/or to receive a trained calibration model 128 from a machine learning computing system 150 (e.g., FIG. 4 shows the "training stage") while FIG. 3 illustrates operation of the controller 102 to use the calibration model 128 to actively convert automatic field measurement data to agronomy data (e.g., FIG. 3 shows "inference stage"). However, as noted elsewhere herein, the calibration model 128 is not required to be a machine-learned model and may, in some embodiments, be a "hand-crafted" heuristic or impose a hand-crafted relationship.

Referring first to FIG. 3, in general, the controller 102 may correspond to any suitable processor-based device(s), such as a computing device or any combination of computing devices. Thus, as shown in FIG. 3, the controller 102 may generally include one or more processor(s) 110 and associated memory devices 112 configured to perform a variety of computer-implemented functions (e.g., performing the methods, steps, algorithms, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory 112 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory 112 may generally be configured to store information accessible to the processor(s) 110, including data 114 that can be retrieved, manipulated, created and/or stored by the processor(s) 110 and instructions 116 that can be executed by the processor(s) 110.

In several embodiments, the data 114 may be stored in one or more databases. For example, the memory 112 may include a sensor data database 118 for storing sensor data received from the sensors 121. For example, the sensors 121 may be configured to continuously or periodically generate sensor data descriptive of adjacent portion(s) of the field as an operation is being performed with the field. In such an embodiment, the sensor data transmitted to the controller 102 from the sensors 121 may be stored within the sensor data database 118 for subsequent processing and/or analysis. It should be appreciated that, as used herein, the term sensor data may include any suitable type of data received from sensors, including image data received from the imaging device(s) 104 that allows for the crop residue coverage of a field to be analyzed, including photographs and other image-related data (e.g., scan data and/or the like).

Additionally, as shown in FIG. 3, the memory 12 may include a measurement data database 120 for storing measurement data (e.g., automatic field measurement data and/or converted agronomy data) for the field being processed. For example, as indicated above, based on the sensor data received from the sensors 121, the controller 102 may be configured to generate field measurement data associated with the field and can re-calibrate the field measurement data to agronomy data that complies with one or more agronomy metrics. The field measurement data and/or the agronomy data may be stored within the measurement data database 120 for subsequent processing, use, and/or analysis.

Moreover, in several embodiments, the memory 12 may also include a location database 122 storing location information about the work vehicle/implement 10, 12 and/or information about the field being processed (e.g., a field map). Specifically, as shown in FIG. 3, the controller 102 may be communicatively coupled to a positioning device(s) 124 installed on or within the work vehicle 10 and/or on or within the implement 12. For example, in one embodiment, the positioning device(s) 124 may be configured to determine the exact location of the work vehicle 10 and/or the implement 12 using a satellite navigation position system (e.g. a GPS system, a Galileo positioning system, the Global Navigation satellite system (GLONASS), the BeiDou Satellite Navigation and Positioning system, and/or the like). In such an embodiment, the location determined by the positioning device(s) 124 may be transmitted to the controller 102 (e.g., in the form coordinates) and subsequently stored within the location database 122 for subsequent processing and/or analysis.

Additionally, in several embodiments, the location data stored within the location database 122 may also be correlated to the sensor data stored within the sensor data database 118. For instance, in one embodiment, the location coordinates derived from the positioning device(s) 124 and the sensor data captured by the sensors 121 may both be time-stamped. In such an embodiment, the time-stamped data may allow sensor data captured by the sensors 121 to be matched or correlated to a corresponding set of location coordinates received from the positioning device(s) 124, thereby allowing the precise location of the portion of the field described by a given set of sensor data to be known (or at least capable of calculation) by the controller 102.

Moreover, by matching sensor data to a corresponding set of location coordinates, the controller 102 may also be configured to generate or update a corresponding field map associated with the field being processed. For example, in instances in which the controller 102 already includes a field map stored within its memory 112 that includes location coordinates associated with various points across the field, sensor data captured by the imaging device(s) 104 may be mapped or correlated to a given location within the field map. Alternatively, based on the location data and the associated sensor data, the controller 102 may be configured to generate a field map for the field that includes the geo-located sensor data associated therewith.

Referring still to FIG. 3, in several embodiments, the instructions 116 stored within the memory 112 of the controller 102 may be executed by the processor(s) 110 to implement a measurement analysis module 126. In general, the measurement analysis module 126 may be configured to analyze the sensor data 118 to determine the measurement data 120. Further, as will be discussed further below, the measurement analysis module 126 can cooperatively operate with or otherwise leverage a calibration model 128 to convert the measurement data 120 from an automatic system metric to an agronomy metric. As an example, the measurement analysis module 126 can perform some or all of method 200 of FIG. 5. Although the measurement analysis module 126 is described as performing both generation of automatic field measurement data and conversion of automatic field measurement data to agronomy data, in some embodiments, these operations are performed by separate components or modules.

Moreover, as shown in FIG. 3, the instructions 116 stored within the memory 112 of the controller 102 may also be executed by the processor(s) 110 to implement a calibration model 128. The calibration model 128 can describe or apply a relationship between the automatic system metric associated with the automatic field measurement system and an agronomy metric, where the agronomy metric is different from the automatic system metric.

The calibration model 128 can have a number of different forms or structures. As one example, the calibration model 128 can perform or include a least squares polynomial fit that describes the relationship between the automatic system metric and the agronomy metric according to a polynomial expression. As another example, the calibration model 128 can include or use a look up table that provides an agronomy data value for each possible field measurement data value. As yet another example, the calibration model 128 can perform or include a Gaussian Process regression that describes the relationship between the automatic system metric and the agronomy metric As another example, the calibration model 128 can be or include a spline or otherwise piece-wise function that describes the relationship between the automatic system metric and the agronomy metric. As yet another example, the calibration model 128 can convert field measurement data expressed according to a logarithmic scale into agronomy data expressed according to a linear scale. In yet another example, the calibration model 128 can perform rounding to discrete output values (e.g., Input 11.23% to Output 10%).

Referring still to FIG. 3, the instructions 116 stored within the memory 112 of the controller 102 may also be executed by the processor(s) 110 to implement a control module 129. In general, the control module 129 may be configured to adjust the operation of the work vehicle 10 and/or the implement 12 by controlling one or more components of the implement/vehicle 12, 10. Specifically, in several embodiments, when the agronomy data values determined by the measurement analysis module 126 differ from target or desired values, the control module 129 may be configured to adjust the operation of the work vehicle 10 and/or the implement 12 in a manner designed to modify the outcome of the operation of the work vehicle 10 and/or the implement 12. For instance, when it is desired to have a percent soil roughness coverage of 30%, the control module 129 may be configured to adjust the operation of the work vehicle 10 and/or the implement 12 so as to increase or decrease the amount of soil roughness remaining in the field when the estimated percent soil roughness coverage for a given imaged portion of the field (or an average estimated percent soil roughness coverage across multiple imaged portions of the field) differs from the target percentage.

In one example, one or more sensors 121 (e.g., imaging devices 104) can be forward-looking image devices that collect sensor data descriptive of upcoming portions of the field. The measurement analysis module 126 can analyze the sensor to determine automatic field measurement data for such upcoming portions of the field. The measurement analysis module 126 can use the calibration model 128 to convert the automatic field measurement data into agronomy data. The control module 129 can adjust the operation of the work vehicle 10 and/or the implement 12 based on the agronomy data for such upcoming portions of the field. Thus, the system 100 can proactively manage various operational parameters of the work vehicle 10 and/or the implement 12 to account for upcoming field conditions in upcoming portions of the field. For example, if an upcoming portion of the field has a larger-than-average soil roughness percentage, then the controller 102 can, in anticipation of reaching such section, modify the operational parameters to account for such larger-than-average soil roughness and vice versa for portions with less-than-average soil roughness.

In another example which may be additional or alternative to the example provided above, one or more sensors 121 (e.g., imaging devices 104) can be rearward-looking image devices that collect sensor data descriptive of receding portions of the field that the work vehicle 10 and/or implement 12 has recently operated upon. The measurement analysis module 126 can analyze the sensor data to determine automatic field measurement data for such receding portions of the field. The measurement analysis module 126 can use the calibration model 128 to convert the automatic field measurement data into agronomy data. The control module 129 can adjust the operation of the work vehicle 10 and/or the implement 12 based on the agronomy data for such receding portions of the field. Thus, the system 100 can reactively manage various operational parameters of the work vehicle 10 and/or the implement 12 based on observed outcomes associated with current settings of such operational parameters. That is, the system 100 can observe the outcome of its current settings and can adjust the settings if the outcome does not match a target outcome.

It should be appreciated that the controller 102 may be configured to implement various different control actions to adjust the operation of the work vehicle 10 and/or the implement 12 in a manner that increases or decreases various field conditions in the field. In one embodiment, the controller 102 may be configured to increase or decrease the operational or ground speed of the implement 12 to affect an increase or decrease certain field conditions such as percent crop residue cover and/or soil roughness. For instance, as shown in FIG. 3, the controller 102 may be communicatively coupled to both the engine 22 and the transmission 24 of the work vehicle 10. In such an embodiment, the controller 102 may be configured to adjust the operation of the engine 22 and/or the transmission 24 in a manner that increases or decreases the ground speed of the work vehicle 10 and, thus, the ground speed of the implement 12, such as by transmitting suitable control signals for controlling an engine or speed governor (not shown) associated with the engine 22 and/or transmitting suitable control signals for controlling the engagement/disengagement of one or more clutches (not shown) provided in operative association with the transmission 24.

In some embodiments, the implement 12 can communicate with the work vehicle 10 to request or command a particular ground speed and/or particular increase or decrease in ground speed from the work vehicle 10. For example, the implement 12 can include or otherwise leverage an ISOBUS Class 3 system to control the speed of the work vehicle 10.

Increasing the ground speed of the vehicle 10 and/or implement 12 may result in a relative increase in the amount of soil roughness and/or crop residue remaining in the field (e.g., relative to the amount remaining absent such increase in ground speed). Likewise, decreasing the ground speed of the vehicle 10 and/or the implement 12 may result in a relative decrease in the amount of soil roughness and/or crop residue remaining in the field (e.g., relative to the amount remaining absent such decrease in ground speed).

In addition to the adjusting the ground speed of the vehicle/implement 10, 12 (or as an alternative thereto), the controller 102 may also be configured to adjust an operating parameter associated with the ground-engaging tools of the implement 12. For instance, as shown in FIG. 3, the controller 102 may be communicatively coupled to one or more valves 130 configured to regulate the supply of fluid (e.g., hydraulic fluid or air) to one or more corresponding actuators 56, 58, 60 of the implement 12. In such an embodiment, by regulating the supply of fluid to the actuator(s) 56, 58, 60, the controller 102 may automatically adjust the relative positioning, penetration depth, down force, and/or any other suitable operating parameter associated with the ground-engaging tools of the implement 12. Increasing the penetration depth or down force of the ground-engaging tools may result in a relative decrease in the amount of soil roughness and/or crop residue remaining in the field (e.g., relative to the amount remaining absent such increase in penetration depth or down force). Likewise, decreasing the penetration depth or down force of the ground-engaging tools may result in a relative increase in the amount of soil roughness and/or crop residue remaining in the field (e.g., relative to the amount remaining absent such decrease in penetration depth or down force).

Referring now to FIG. 4, according to an aspect of the present disclosure, the controller 102 can store or include one or more calibration models 128. In some embodiments, the calibration models 128 can be or can otherwise include various machine-learned models such as a machine-learned regression model; a support vector machine; one or more decision trees; a neural network; and/or other types of models including both linear models and non-linear models.

Example machine-learned regression models perform linear regression, polynomial regression, or nonlinear regression. Example machine-learned regression models can perform simple regression or multiple regression. In some embodiments, a softmax function or layer can be used to squash a set of real values respectively associated with two or more possible outputs to a set of real values in the range (0, 1) that sum to one.

Example neural networks include feed-forward neural networks, recurrent neural networks (e.g., long short-term memory recurrent neural networks), convolutional neural networks, or other forms of neural networks.

However, in some embodiments, the calibration models 128 are not machine-learned but may instead be hand-crafted heuristics or other data structures that enable a conversion from automatic field measurements to agronomy measurements.

In some embodiments in which the calibration models 128 are machine-learned, the controller 102 can receive the one or more calibration models 128 from the machine learning computing system 150 over network 180 and can store the one or more calibration models 128 in the memory 112. The controller 102 can then use or otherwise run the one or more calibration models 128 (e.g., by processor(s) 110).

The machine learning computing system 150 includes one or more processors 152 and a memory 154. The one or more processors 152 can be any suitable processing device such as described with reference to processor(s) 110. The memory 154 can include any suitable storage device such as described with reference to memory 112.

The memory 154 can store information that can be accessed by the one or more processors 152. For instance, the memory 154 (e.g., one or more non-transitory computer-readable storage mediums, memory devices) can store data 156 that can be obtained, received, accessed, written, manipulated, created, and/or stored. In some implementations, the machine learning computing system 150 can obtain data from one or more memory device(s) that are remote from the system 150.

The memory 154 can also store computer-readable instructions 158 that can be executed by the one or more processors 152. The instructions 158 can be software written in any suitable programming language or can be implemented in hardware. Additionally, or alternatively, the instructions 158 can be executed in logically and/or virtually separate threads on processor(s) 152.

For example, the memory 154 can store instructions 158 that when executed by the one or more processors 152 cause the one or more processors 152 to perform any of the operations and/or functions described herein.

In some implementations, the machine learning computing system 150 includes one or more server computing devices. If the machine learning computing system 150 includes multiple server computing devices, such server computing devices can operate according to various computing architectures, including, for example, sequential computing architectures, parallel computing architectures, or some combination thereof.

In addition or alternatively to the model(s) 128 at the controller 102, the machine learning computing system 150 can include one or more calibration models 140. For example, the models 140 can be or can otherwise include various calibration models such as any of the example models described above with reference to models 128.

In some embodiments, the machine learning computing system 150 can communicate with the controller 102 according to a client-server relationship. For example, the machine learning computing system 150 can implement the calibration models 140 to provide a web service to the controller 102. For example, the web service can provide data calibration as a service.

Thus, calibration models 128 can located and used at the controller 102 and/or calibration models 140 can be located and used at the machine learning computing system 150.

In some implementations, the machine learning computing system 150 and/or the controller 102 can train the calibration models 128 and/or 140 through use of a trainer 160. The trainer 160 can train the calibration models 128 and/or 140 using one or more training or learning algorithms. One example training technique is backwards propagation of errors ("backpropagation"). Gradient-based or other training techniques can be used as well.

In some implementations, the trainer 160 can perform supervised training techniques using a set of labeled training data 162. For example, the labeled training data 162 can include a set of field measurement data that is labeled with the "correct" agronomy data that is correctly calibrated to the field measurement data. Thus, the labeled training data can provide examples of inputs and correctly calibrated outputs. In other implementations, the trainer 160 can perform unsupervised training techniques using a set of unlabeled training data 162.

The trainer 160 can perform a number of generalization techniques to improve the generalization capability of the models being trained. Generalization techniques include weight decays, dropouts, or other techniques. The trainer 160 can be implemented in hardware, software, firmware, or combinations thereof.

Furthermore, as indicated above, the calibration models 128 are not required to be machine-learned models but can instead be heuristics or other algorithms or structures that enable conversion from automatic field measurement data to agronomy data, as described herein.

The network(s) 180 can be any type of network or combination of networks that allows for communication between devices. In some embodiments, the network(s) can include one or more of a local area network, wide area network, the Internet, secure network, cellular network, mesh network, peer-to-peer communication link and/or some combination thereof and can include any number of wired or wireless links. Communication over the network(s) 180 can be accomplished, for instance, via a communications interface using any type of protocol, protection scheme, encoding, format, packaging, etc.

FIGS. 3 and 4 illustrate example computing systems that can be used to implement the present disclosure. Other computing systems can be used as well. For example, in some implementations, the controller 102 can include the trainer 160 and the training dataset 162. In such implementations, the calibration models 128 can be both trained and used locally at the controller 102. As another example, in some implementations, the controller 102 is not connected to other computing systems.

Figure 5:
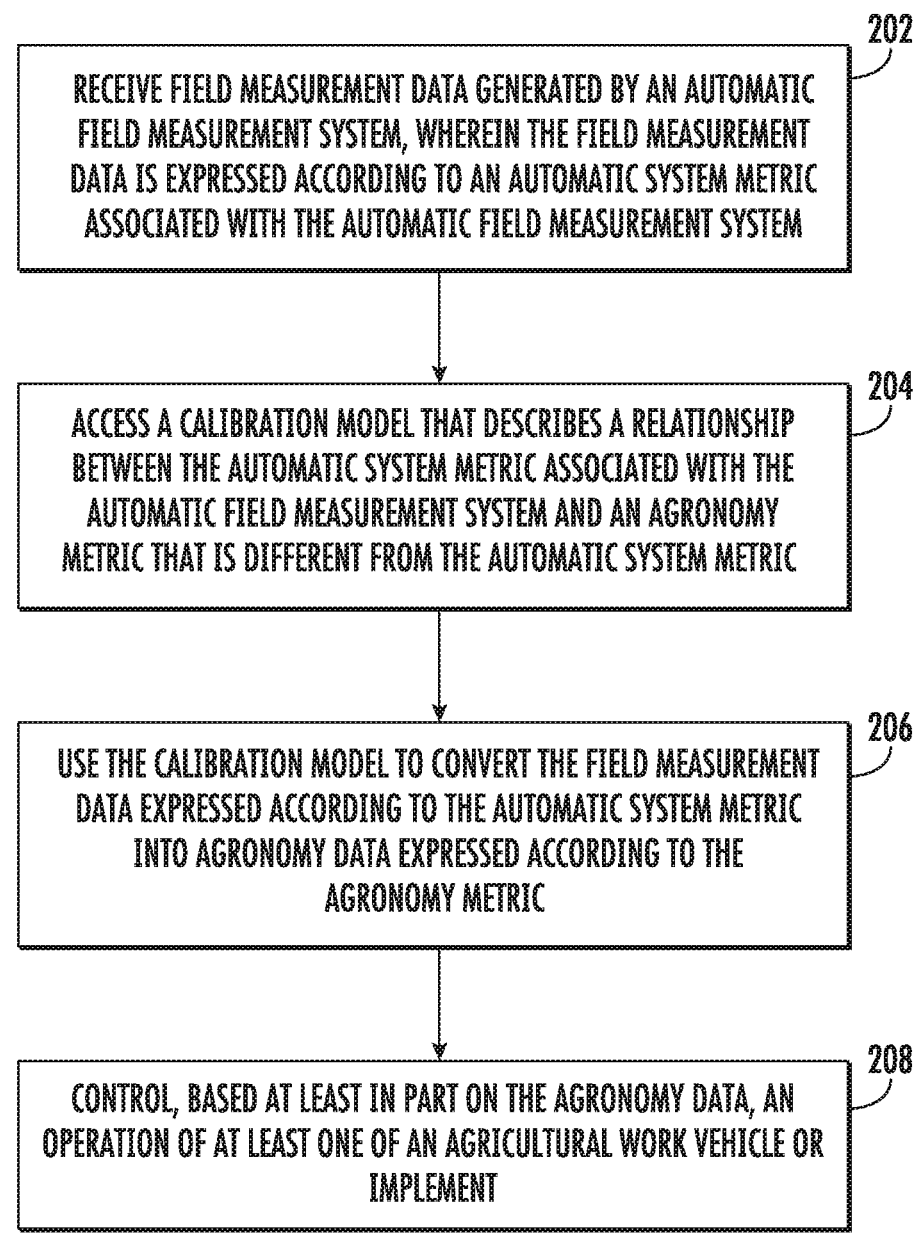
FIG. 5 illustrates a flow diagram of one embodiment of a method for calibrating automatic field measurements in accordance with aspects of the present subject matter.

Referring now to FIG. 5, a flow diagram of one embodiment of a method 200 for calibrating automatic field measurements is illustrated in accordance with aspects of the present subject matter. In general, the method 200 will be described herein with reference to the work vehicle 10 and the implement 12 shown in FIGS. 1 and 2, as well as the various system components shown in FIGS. 3 and/or 4. However, it should be appreciated that the disclosed method 200 may be implemented with work vehicles and/or implements having any other suitable configurations and/or within systems having any other suitable system configuration. In addition, although FIG. 5 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 5, at (202), the method 200 may include receiving field measurement data generated by an automatic field measurement system. The field measurement data generated by the automatic field measurement system can be expressed according to an automatic system metric associated with the automatic field measurement system. For example, as indicated above, the measurement analysis module 126 of the controller 102 may be configured to generate the automatic field measurement data from sensor data. As examples, the field measurement data may be crop residue cover data descriptive of crop residue in a field and/or soil roughness data.

At (204), the method 200 may include accessing, with the computing device, a calibration model that describes a relationship between the automatic system metric associated with the automatic field measurement system and an agronomy metric that is different from the automatic system metric. For example, the measurement analysis module 126 can access the calibration model 128.

The calibration model accessed at (204) can have a number of different forms or structures. As one example, the calibration model can perform or include a least squares polynomial fit that describes the relationship between the automatic system metric and the agronomy metric according to a polynomial expression. As another example, the calibration model can include or use a look up table that provides an agronomy data value for each possible field measurement data value. As yet another example, the calibration model can perform or include a Gaussian Process regression that describes the relationship between the automatic system metric and the agronomy metric As another example, the calibration model can be or include a spline or otherwise piece-wise function that describes the relationship between the automatic system metric and the agronomy metric. As yet another example, the calibration model can convert field measurement data expressed according to a logarithmic scale into agronomy data expressed according to a linear scale.

In some embodiments, the automatic system metric can include the field measurement data expressed according to a logarithmic scale while the agronomy metric can include the agronomy data expressed according to a linear scale.

At (206), the method 200 may include using the calibration model to convert the field measurement data expressed according to the automatic system metric into agronomy data expressed according to the agronomy metric. For example, the measurement analysis module 126 can use the calibration model 128 to convert the field measurement data expressed according to the automatic system metric into agronomy data expressed according to the agronomy metric.

At (208), the method 200 may include controlling, based at least in part on the agronomy data, an operation of at least one of an agricultural work vehicle or implement. For example, as indicated above, the control module 129 of the controller 102 of the disclosed system 100 may be configured to control the operation of the work vehicle 10 and/or the implement 12, such as by controlling one or more components of the work vehicle 10 and/or the implement 12 to allow an operation to be performed within the field (e.g., a tillage operation).

In some embodiments, both the automatic field measurement system and the computing system implementing method 200 are physically located on-board the at least one of the agricultural work vehicle or implement.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A computer-implemented method for calibrating automatic field measurements, the method comprising:
receiving, with a computing device, field measurement data generated by an automatic field measurement system, wherein the field measurement data generated by the automatic field measurement system is expressed according to an automatic system metric associated with the automatic field measurement system, the field measurement data being associated with a field;
accessing, with the computing device, a calibration model that describes a relationship between the automatic system metric associated with the automatic field measurement system and an agronomy metric, wherein the agronomy metric is different from the automatic system metric;
using, with the computing device, the calibration model to convert the field measurement data expressed according to the automatic system metric into agronomy data expressed according to the agronomy metric; and
controlling, with the computing device and based at least in part on the agronomy data, an operation of at least one of an agricultural work vehicle or an implement within the field.

2. The computer-implemented method of claim 1, wherein both the automatic field measurement system and the computing device are physically located on-board the at least one of the agricultural work vehicle or the implement.

3. The computer-implemented method of claim 1, wherein:
accessing, with the computing device, the calibration model comprises accessing, with the computing device, a least squares polynomial fit that describes the relationship between the automatic system metric and the agronomy metric according to a polynomial expression; and
using, with the computing device, the calibration model comprises using, with the computing device, the least squares polynomial fit to convert the field measurement data expressed according to the automatic system metric into agronomy data expressed according to the agronomy metric.

4. The computer-implemented method of claim 1, wherein:
accessing, with the computing device, the calibration model comprises accessing, with the computing device, a look up table that provides an agronomy data value for each possible field measurement data value; and
using, with the computing device, the calibration model comprises using, with the computing device, the look up table to convert the field measurement data expressed according to the automatic system metric into agronomy data expressed according to the agronomy metric.

5. The computer-implemented method of claim 1, wherein:
accessing, with the computing device, the calibration model comprises accessing, with the computing device, a Gaussian Process regression that describes the relationship between the automatic system metric and the agronomy metric; and
using, with the computing device, the calibration model comprises using, with the computing device, the Gaussian Process regression to convert the field measurement data expressed according to the automatic system metric into agronomy data expressed according to the agronomy metric.

6. The computer-implemented method of claim 1, wherein:
accessing, with the computing device, the calibration model comprises accessing, with the computing device, a spline that describes the relationship between the automatic system metric and the agronomy metric; and using, with the computing device, the calibration model comprises using, with the computing device, the spline to convert the field measurement data expressed according to the automatic system metric into agronomy data expressed according to the agronomy metric.

7. The computer-implemented method of claim 1, wherein the field measurement data comprises crop residue cover data descriptive of crop residue in the field.

8. The computer-implemented method of claim 7, wherein the automatic system metric comprises the field measurement data expressed according to a logarithmic scale and wherein the agronomy metric comprises the agronomy data expressed according to a linear scale.

9. The computer-implemented method of claim 1, wherein the field measurement data comprises soil roughness data.

10. A computing system for calibrating automatic field measurements, the computing system comprising:
one or more processors; and
one or more non-transitory computer-readable media that collectively store:
a calibration model that describes a relationship between an automatic system metric associated with an automatic field measurement system and an agronomy metric, wherein the agronomy metric is different from the automatic system metric; and
instructions that, when executed by the one or more processors, cause the computing system to perform operations, the operations comprising:
receiving field measurement data generated by the automatic field measurement system, wherein the field measurement data generated by the automatic field measurement system is expressed according to the automatic system metric associated with the automatic field measurement system, the field measurement data being associated with a field;
accessing the calibration model that describes the relationship between the automatic system metric associated with the automatic field measurement system and the agronomy metric;
using the calibration model to convert the field measurement data expressed according to the automatic system metric into agronomy data expressed according to the agronomy metric; and
controlling, based at least in part on the agronomy data, an operation of at least one of a work vehicle located in the field or an implement towed by the work vehicle across the field.

11. The computing system of claim 10, wherein the computing system further comprises the automatic field measurement system configured to generate the field measurement data.

12. The computing system of claim 10, wherein both the automatic field measurement system and the computing system are physically located on-board the at least one of the work vehicle or the implement.

13. The computing system of claim 10, wherein:
accessing the calibration model comprises accessing a least squares polynomial fit that describes the relationship between the automatic system metric and the agronomy metric according to a polynomial expression; and
using the calibration model comprises using the least squares polynomial fit to convert the field measurement data expressed according to the automatic system metric into agronomy data expressed according to the agronomy metric.

14. The computing system of claim 10, wherein:
accessing the calibration model comprises accessing a look up table that provides an agronomy data value for each possible field measurement data value; and
using the calibration model comprises using the look up table to convert the field measurement data expressed according to the automatic system metric into agronomy data expressed according to the agronomy metric.

15. The computing system of claim 10, wherein:
accessing the calibration model comprises accessing a Gaussian Process regression that describes the relationship between the automatic system metric and the agronomy metric; and
using the calibration model comprises using the Gaussian Process regression to convert the field measurement data expressed according to the automatic system metric into agronomy data expressed according to the agronomy metric.

16. The computing system of claim 10, wherein:
accessing the calibration model comprises accessing a spline that describes the relationship between the automatic system metric and the agronomy metric; and
using the calibration model comprises using the spline to convert the field measurement data expressed according to the automatic system metric into agronomy data expressed according to the agronomy metric.

17. The computing system of claim 16, wherein the automatic system metric comprises the field measurement data expressed according to a logarithmic scale and wherein the agronomy metric comprises the agronomy data expressed according to a linear scale.

18. An agricultural system, comprising:
a work vehicle;
an implement configured to be towed by the work vehicle across a field;
an automatic field measurement system configured to generate field measurement data descriptive of an agricultural field, wherein the field measurement data generated by the automatic field measurement system is expressed according to an automatic system metric associated with the automatic field measurement system, the field measurement data being associated with the field; and
a calibration computing system configured to:
receive the field measurement data generated by the automatic field measurement system;
access a calibration model that describes a relationship between the automatic system metric associated with the automatic field measurement system and an agronomy metric, wherein the agronomy metric is different from the automatic system metric;
use the calibration model to convert the field measurement data expressed according to the automatic system metric into agronomy data expressed according to the agronomy metric; and
control, based at least in part on the agronomy data, an operation of at least one of the work vehicle or the implement.

19. The agricultural system of claim 18, wherein the automatic field measurement system is physically located on-board the work vehicle or the implement.

* * * * *